United States Patent [19]

Tseng

[11] Patent Number: 5,551,152
[45] Date of Patent: * Sep. 3, 1996

[54] SHAVING SYSTEM

[75] Inventor: Mingchih M. Tseng, Hingham, Mass.

[73] Assignee: The Gillette Company, Boston, Mass.

[*] Notice: The portion of the term of this patent subsequent to Sep. 27, 2011, has been disclaimed.

[21] Appl. No.: 311,726

[22] Filed: Sep. 23, 1994

Related U.S. Application Data

[63] Continuation of Ser. No. 865,594, Apr. 9, 1992, Pat. No. 5,349,750, which is a continuation of Ser. No. 590,027, Sep. 28, 1990, abandoned.

[51] Int. Cl.$^6$ .............................. B26B 21/44; B26B 21/14
[52] U.S. Cl. .............................. 30/41; 30/32; 30/50; 30/90
[58] Field of Search .............................. 30/32, 41, 41.5, 30/50, 90

[56] References Cited

U.S. PATENT DOCUMENTS

| | | | |
|---|---|---|---|
| 4,069,580 | 1/1978 | Cartwright et al. | 30/32 X |
| 4,112,989 | 9/1978 | Grode et al. | 150/1 |
| 4,170,821 | 10/1979 | Booth | 30/41 |
| 4,586,255 | 5/1986 | Jacobson | 30/41 |
| 4,621,424 | 11/1986 | Jacobson | 30/41 |
| 4,624,051 | 11/1986 | Apprille, Jr. et al. | 30/50 |
| 4,777,722 | 10/1988 | Trotta | 30/90 X |
| 4,778,640 | 10/1988 | Braun et al. | 264/250 |
| 4,872,263 | 10/1989 | Etheridge | 30/41 |
| 4,875,287 | 10/1989 | Creasy | 30/41 X |
| 4,916,814 | 4/1990 | Althaus | 30/50 X |

FOREIGN PATENT DOCUMENTS

| | | | |
|---|---|---|---|
| 0276094 | 7/1988 | European Pat. Off. | |
| 0287387 | 10/1988 | European Pat. Off. | |
| 2024082 | 5/1982 | United Kingdom | 30/41 |

*Primary Examiner*—Jack W. Lavinder
*Assistant Examiner*—Jay A. Stelacone
*Attorney, Agent, or Firm*—Fish & Richardson P.C.

[57] ABSTRACT

A shaving system having a blade and support structure that define external skin engaging surfaces in front of and to the rear of the cutting edge of the blade, the support structure including a shaving aid composite comprised of a blend of ethylene vinyl acetate and a shaving aid composition adjacent the cutting edge of the blade.

16 Claims, 1 Drawing Sheet

SHAVING SYSTEM

This is a continuation of application Ser. No. 07/865,594, filed Apr. 9, 1992, now U.S. Pat. No. 5,349,750, which in turn is a continuation of Ser. No. 07/590,027 filed Sept. 28, 1990, now abandoned.

This invention relates to shaving systems, and more particularly to shaving systems of the wet shave type.

In shaving systems of the wet shave type, factors such as the frictional drag of the razor across the skin, the force needed to sever hairs, and irritation of pre-existing skin damage can create a degree of shaving discomfort. Discomfort, and other problems accompanying wet shaving systems, can be alleviated by the application of shaving aids to the skin. Shaving aids may be applied prior to, during, or after shaving. A number of problems accompany the use of pre- and post-applied shaving aids. Pre-applied-shaving aids can evaporate or can be carried away from the site of application by repeated strokes of the razor. Post-applied-shaving aids are not present on the skin during shaving and thus their application may be to late to prevent an unwanted affect. Both pre-applied and post-applied shaving aids add additional steps to the shaving process.

Proposals have been made to incorporate a shaving aid e.g., lubricant, whisker softener, razor cleanser, medicinal agent, cosmetic agent or combination thereof, into a razor, e.g., by depositing a shaving aid in a recess on the razor, by incorporating a shaving aid directly into one or more molded polymeric components of the razor, by adhesively securing a shaving aid composite to the razor, and by use of a mechanical connection between a shaving aid composite and the razor. A water-soluble shaving aid, e.g. polyethylene oxide, has been mixed with non-water-soluble material, e.g., a polystyrene polymer, to form an insoluble polymer/soluble shaving aid composite. The composite has been mounted on razor and shaving cartridge structures, adjacent the shaving edge or edges, of single or multiple blade shaving system. Upon exposure to water, the water-soluble shaving aid leaches from the composite onto the skin.

In accordance with one aspect of the invention, there is provided a shaving unit that comprises at least one blade and a shaving aid composite that has a surface for engaging the user's skin adjacent the blade edge or edges. The shaving unit may be of the disposable cartridge type adapted for coupling to and uncoupling from a razor handle or may be integral with a handle so that the complete razor is discarded as a unit when the blade or blades become dulled. The blade edge (or edges) cooperate with skin engaging surfaces to define shaving geometry. The shaving aid composite is a matrix of water insoluble ethylene vinyl acetate (EVA—a copolymer of ethylene and vinyl acetate) and an effective amount of one or more shaving aids disposed in the ethylene vinyl acetate matrix and which leaches out with water polyethylene oxide. The shaving aid composite can also be a mixture of ethylene vinyl acetate and an effective amount of one or more water-insoluble shaving aid (e.g., silicone copolymer or polytetrafluoroethylene (Teflon) powder) and preferably has a skin engaging surface.

Ethylene vinyl acetate is a copolymer of ethylene and vinyl acetate and is available commercially from a number of sources. The properties of an ethylene vinyl acetate copolymer depend in large part on the percentage of vinyl acetate it contains. Commercial grades of ethylene vinyl acetate range in vinyl acetate content from five to fifty weight percent and range in melt index from 0.3 to 43 g/min, in hardness from 73 Shore A to 98 Shore A or 24 Shore D to 47 Shore D, and in Vicat softening temperature from 80° C. to 36° C. Increasing the amount of vinyl acetate in an ethylene vinyl acetate copolymer reduces its crystallinity, increases its flexibility and reduces its hardness.

An ethylene vinyl acetate copolymer containing twenty five weight percent vinyl acetate forms shaving aid composites with an improved combination of leach rate, flexibility, softness, strength, abrasion resistance, resistance to cracking, softening temperature attributes, and processability. In particular embodiments the shaving aid composite contains between ten percent and fifty percent by weight ethylene vinyl acetate and between fifty percent and ninety percent by weight shaving aid material. Suitable water-soluble and non-water soluble shaving aid materials include, for example, polyethylene oxide, polyvinyl pyrrolidone, polyacrylamide, hydroxypropyl cellulose, polyvinyl imidazonline, polyhydroxyethylmethacrylate, silicone copolymers and sucrose stearate, vitamin E. Panthenol, aloe, essential oils and other moisturizers and soothing agents. The proportions may be varied but the composite preferably includes at least fifty percent of water-soluble shaving aid materials. In particular embodiments, the shaving aid composite includes additives such as color dyes and bactericides in minor amounts.

The low softening temperature of ethylene vinyl acetate copolymers allows lower processing temperatures in the production of shaving aid composites. Elvax 360 (Dupont), a commercial ethylene vinyl acetate copolymer containing twenty-five percent vinyl acetate, has a Vicat softening temperature of 53° C., which is approximately 40° C. below that of polystyrene. Shaving aid composites formed from ethylene vinyl acetate copolymers can be molded, extruded, or otherwise manufactured at lower temperatures than those used for other insoluble polymers, such as polystyrene with resulting reduced thermal degradation of shaving aid material and other functional additives, such as polyethylene oxide, silicone, plasticizers, moisturizers, perfumes, and vitamins. The ethylene vinyl acetate copolymer may also act as a hot melt adhesive thus providing a simple and effective means of attaching the shaving aid composite to razor structure.

Particular embodiments include shaving aid composites of the following compositions: twenty-five percent by weight ethylene vinyl acetate (twenty-five percent vinyl acetate) and seventy-five percent by weight polyethylene oxide, (this shaving aid composite can be molded or extruded at approximately 100°–140° C.); seventy percent by weight ethylene vinyl acetate (twenty-five percent vinyl acetate) and thirty percent by weight silicone copolymer (this shaving aid composite can be extruded at approximately 100° C.); eighteen percent by weight ethylene vinyl acetate (twenty-five percent vinyl acetate), seventy-seven percent by weight polyethylene oxide, and five percent by weight sucrose stearate (this shaving aid composite can be molded at approximately 130° C.); and twenty-four percent by weight ethylene vinyl acetate (twenty-five percent vinyl acetate), seventy-two percent by weight polyethylene oxide, and four percent by weight silicone wax (this shaving aid composite may be molded at approximately 130° C.). Extrusion and molding temperatures and pressures vary with the particular polymers used.

The nature and relative proportions of the water-soluble and non-water soluble components and water insoluble ethylene vinyl acetate in the polymer blend should be such that the shaving aid composite has adequate mechanical strength, both as initially produced and after a significant amount of the water-soluble material has been leached out, the quantity of the water-soluble material being sufficient to provide effective shaving assistance, such as lubrication, for the entire expected life of the blade or blades. In case of a water-soluble component contained in the shaving aid composite, comfortable and effective shaving can be obtained by wetting the shaving area with water prior to shaving. The water present on the shaving area leaches out a proportion of the water-soluble material for delivery to the skin surface.

Shaving aid composites of ethylene vinyl acetate copolymers with appropriate vinyl acetate content are soft, flexible, resilient, display excellent resistance to cracking, and release water-soluble shaving aids in relatively linear fashion. A shaving system with such a shaving aid composite results in a product that possesses an attractive appearance and that produces a comfortable shave.

Other features and advantages will be seen as the following description of particular embodiments progresses, in conjunction with the drawings, in which.

DESCRIPTION OF PARTICULAR EMBODIMENTS

Figure 1:
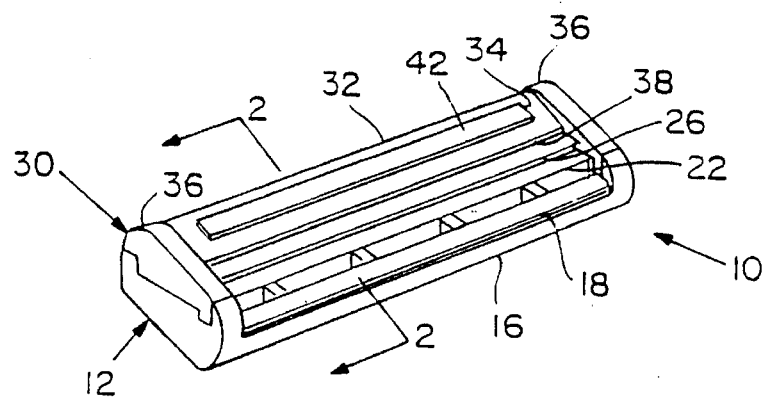
FIG. 1 is a perspective view of a razor unit in accordance with the invention.
Figure 2:
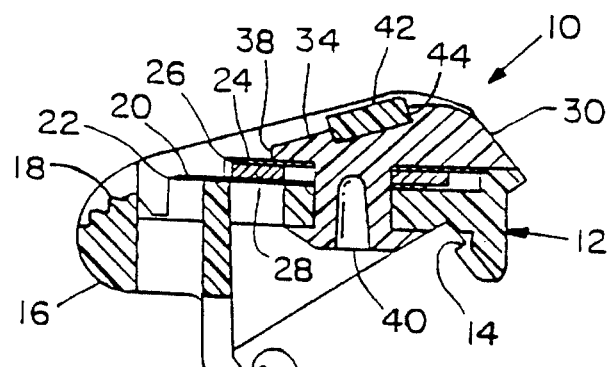
FIG. 2 is a sectional view taken along the line 2—2 of FIG. 1.

The shaving unit 10 shown in FIGS. 1 and 2 includes base or platform member 12 molded of high impact polystyrene that includes integral coupling groove structure 14 for attachment to a razor handle and guard structure 16 that defines a transversely extending forward skin engaging surface 18. On the upper surface of platform 12 are disposed steel leading blade 20 having a sharpened edge 22, steel following blade 24 having sharpened edge 26, and aluminum spacer member 28 that maintains blades 20 and 24 in spaced relation. Cap member 30 is molded of high impact polystyrene and has body portion 32 that defines skin engaging surface 34 that extends transversely between forwardly projecting end walls 36 and has a front edge 38 that is disposed rearwardly of blade edge 26. Integral rivet portions 40 extend downwardly from transversely extending body portion 32 and pass through holes in blades 20 and 24, spacer 28, and platform 12 to secure cap 30, blades 20, 24 and spacer 28 on platform 12. Affixed to skin engaging surface 34 is shaving aid composite 42.

Figure 3:
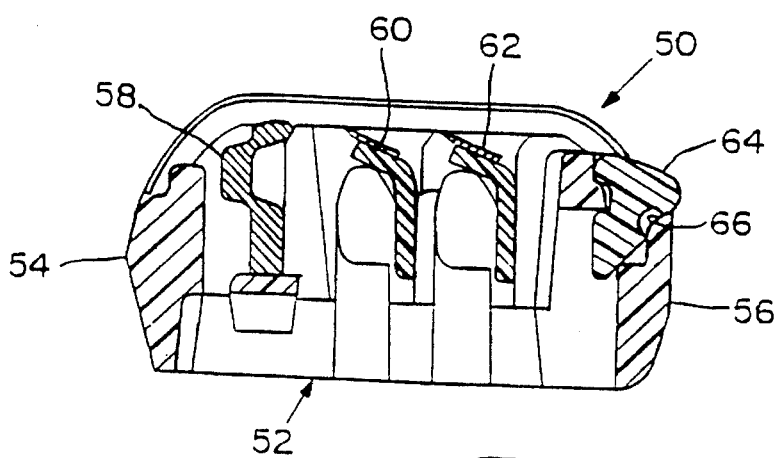
FIG. 3 is a perspective view of another razor unit in accordance with the invention.

The shaving unit 50 shown in FIG. 3 is of the type shown in Jacobson U.S. Pat. No. 4,586,255 and includes body 52 with front portion 54 and rear portion 56. Resiliently secured in body 52 are guard member 58, leading blade unit 60 and trailing blade unit 62. A shaving aid composite in the form of elongated insert member 64 is frictionally locked in opening 66 of rear portion 56.

The following examples show by way of illustration and not by way of limitation practice of the invention.

EXAMPLE 1

A blend is formed of eighty percent by weight of polyethylene oxide (specifically a mixture of forty-eight weight percent Polyox Coagulant polyethylene oxide—five million molecular weight percent Polyox N-750 polyethylene oxide—300,000 molecular weight—the polyethylene oxide of the ultimate blend having a molecular weight of about 3.5 million); twenty percent by weight of ethylene vinyl acetate (twenty-five percent vinyl acetate) (Elvax 360) and color dye and bactericide additives in minor amounts. The blend is extruded at a temperature of about 120° C. to form a strip of shaving aid composite material. Member 42 is sliced from the extruded strip and secured in recess 44. In similar manner, the blend is extruded to form inserts 64 which are secured in openings 66 of shaving units 50. The resulting cartridge possess good overall shaving performance.

EXAMPLE 2

A blend is formed of forty-three percent by weight of polyethylene oxide (five million average molecular weight), thirty-two percent by weight polyethylene oxide (300,000 average molecular weight), and twenty-five percent by weight of water insoluble ethylene vinyl acetate (Elvax 360), The blend is extruded at a temperature of about 115° C. to form a strip. Members 42 are sliced from extruded strip and secured to shaving cartridges. The cartridges provide excellent shaving comfort and are significantly better in overall shaving performance than blends of polystyrene and similar polyethylene oxide proportions.

EXAMPLE 3

A blend of eighty percent by weight of ethylene vinyl acetate copolymer (containing twenty-five percent vinyl acetate) and twenty percent by weight of silicone copolymer (e.g. Trimethylsiloxysilicate) is extruded at approximately 100° C. Members 42 and 64 are sliced from extruded strip and secured to the caps of razor cartridges 10 and 50. The resulting razor cartridges possess good overall shaving performance.

EXAMPLE 4

A blend of eighteen percent ethylene vinyl acetate (twenty-five percent vinyl acetate); five percent sucrose stearate; and seventy-seven percent by weight of a water-soluble polymer (a mixture of forty percent by weight of Polyox Coagulant polyethylene oxide and forty percent by weight of Polyox WSRN-750 polyethylene oxide) is molded at a temperature of 130° C. to form members 42 and inserts 64. The resulting shaving aid composite members are secured to their respective razor structures 10, 50 and the resulting razor structures exhibits good shaving performance.

EXAMPLE 5

A mixture of twenty-four percent by weight ethylene vinyl acetate (twenty-five percent vinyl acetate); forty-three percent by weight of Polyox Coagulant polyethylene oxide; twenty-nine percent by weight Polyox WSRN-750 polyethylene oxide; and four percent by weight silicone wax is molded at a temperature of 130° C. The same mixture is extruded at a temperature of 110° C. and attached to razors. The resulting shaving aid composites 42, 64 are soft, flexible, resilient, and show excellent resistance to cracking, and shave tests indicate that the resulting razors have excellent shaving characteristics.

Shaving units 10, 50 are used in conventional manner (typically in conjunction with a shaving cream or gel) with polyethylene oxide and/or other shaving aid material being dispensed from member 42, 64 during shaving. With each stroke of the razor, shaving aid material is immediately applied to the skin and thus provides shaving aid material that is continually renewed during shaving operations over the useful life of shaving units 10, 50.

While particular embodiments of the invention have been shown and described, various modifications will be apparent to those skilled in the art and therefore it is not intended that the invention be limited to the disclosed embodiment or to details thereof and departures may be made therefrom within the spirit and scope of the invention.

What is claimed is:

1. A shaving system of the wet shave type comprising a blade member having a shaving edge, and structure defining an external skin-engaging portion adjacent the shaving edge of said blade member, said skin-engaging portion consisting essentially of a composite includes a mixture of ethylene vinyl acetate and of a shaving aid.

2. The shaving system of claim 1 wherein said ethylene vinyl acetate contains between five and fifty weight percent vinyl acetate.

3. The shaving system of claim 1 wherein said ethylene vinyl acetate contains approximately twenty-five percent vinyl acetate.

4. The shaving system of claim 1 wherein said composite consists essentially of ten to fifty percent by weight ethylene vinyl acetate and fifty to ninety percent by weight shaving aid.

5. The shaving system of claim 1 wherein said shaving aid is selected from the group consisting of polyethylene oxide, polyvinyl pyrrolidone, polyacrylamide, hydroxypropyl cellulose, polyvinyl imidazonline polyhydroxyethylmethacrylate, silicone copolymers, and sucrose stearate.

6. The shaving system of claim 5 wherein said composite includes about seventy to about ninety percent by weight ethylene vinyl acetate and about ten to about thirty percent by weight of said silicone copolymer.

7. The shaving system of claim 1 wherein said composite is a mixture of material that has been extruded.

8. The shaving system of claim 7 wherein said extruded composite is attached to said external skin-engaging portion rearwardly of said shaving edge.

9. The shaving system of claim 1 wherein said composite is a mixture of material that has been molded.

10. The shaving system of claim 9 wherein said molded composite is attached to said external skin-engaging portion rearwardly of said shaving edge.

11. A shaving system of the wet shave type comprising a blade member having a shaving edge, and structure defining an external skin-engaging portion adjacent the shaving edge of said blade member, said skin-engaging portion including a composite having an exposed, skin-contacting surface comprising a mixture of ethylene vinyl acetate and of a shaving aid.

12. The shaving system of claim 11 wherein said ethylene vinyl acetate contains between five and fifty weight percent vinyl acetate.

13. The shaving system of claim 11 wherein said ethylene vinyl acetate contains approximately twenty-five weight percent vinyl acetate.

14. The shaving system of claim 11 wherein said composite comprises ten to fifty percent by weight ethylene vinyl acetate and fifty to ninety percent by weight shaving aid.

15. The shaving system of claim 11 wherein said composite comprises a blend of ethylene vinyl acetate, high molecular weight polyethylene oxide that has a molecular weight of greater than about three million and low molecular weight polyethylene oxide that has a molecular weight of less than about one million.

16. The shaving system of claim 11 wherein said shaving aid is selected from the group consisting of polyethylene oxide, polyvinyl pyrrolidone, polyacrylamide, hydroxypropyl cellulose, polyvinyl imidazonline polyhydroxyethylmethacrylate, silicone copolymers, and sucrose stearate.

* * * * *

UNITED STATES PATENT AND TRADEMARK OFFICE
CERTIFICATE OF CORRECTION

PATENT NO. : 5,551,152

DATED : September 3, 1996

INVENTOR(S) : Mingchih M. Tseng

It is certified that error appears in the above-identified patent and that said Letters Patent is hereby corrected as shown below:

In col. 1, line 67 to col. 2, line 1, "80° C." should be --80°C--.

In col. 2, line 29, "53° C." should be --53°C--.

In col. 2, line 29, "40° C." should be --40°C--.

In col. 2, line 46, "100°-140° C." should be --100°-140°C--.

In col. 2, line 50, "100° C." should be --100°C--.

In col. 2, line 54, "130° C." should be --130°C--.

In col. 2, line 58, "130° C." should be --130°C--.

In col. 4, line 1, "120° C." should be --120°C--.

In col. 4, lines 15-16, "115° C." should be --115°C--.

In col. 4, line 28, "100° C." should be --100°C--.

In col. 4, line 41, "130° C." should be --130°C--.

UNITED STATES PATENT AND TRADEMARK OFFICE
CERTIFICATE OF CORRECTION

PATENT NO. : 5,551,152
DATED : September 3, 1996
INVENTOR(S) : Mingchih M. Tseng It is certified that error appears in the above-indentified patent and that said Letters Patent is hereby corrected as shown below:

In col. 4, line 54, "130° C." should be --130°C--.

In col. 4, line 55, "110° C." should be --110°C--.

In claim 1, line 12, "includes" should be --including--.

In claim 4, line 21, "consists essentially of" should be --includes--.

Signed and Sealed this

Fourth Day of August, 1998

Attest:

BRUCE LEHMAN

Attesting Officer

Commissioner of Patents and Trademarks